United States Patent
Sandage, Jr. et al.

(10) Patent No.: US 8,637,087 B2
(45) Date of Patent: Jan. 28, 2014

(54) TREATMENT OF INTERSTITIAL CYSTITIS USING (6AR, 10AR)-Δ⁸-TETRAHYDROCANNABINOL-11-OIC ACIDS

(75) Inventors: Bobby W. Sandage, Jr., Acton, MA (US); Glenn L. Cooper, Wayland, MA (US)

(73) Assignee: JB Therapeutics Inc., Newton Center, MA (US)

( * ) Notice: Subject to any disclaimer, the term of this patent is extended or adjusted under 35 U.S.C. 154(b) by 0 days.

(21) Appl. No.: 12/624,313

(22) Filed: Nov. 23, 2009

(65) Prior Publication Data

US 2011/0318425 A1    Dec. 29, 2011

Related U.S. Application Data

(63) Continuation of application No. 12/070,342, filed on Feb. 15, 2008, now abandoned, and a continuation of application No. 11/299,688, filed on Dec. 13, 2005, now abandoned.

(60) Provisional application No. 60/658,578, filed on Mar. 7, 2005, provisional application No. 60/635,005, filed on Dec. 13, 2004.

(51) Int. Cl.
| | | |
|---|---|---|
| *A61K 31/352* | (2006.01) | |
| *A61K 31/437* | (2006.01) | |
| *A61P 23/00* | (2006.01) | |

(52) U.S. Cl.
USPC ........... 424/618; 424/725; 514/455; 514/304; 514/317; 514/305; 514/424; 514/291; 514/256; 514/217; 514/56; 514/454

(58) Field of Classification Search
None
See application file for complete search history.

(56) References Cited

U.S. PATENT DOCUMENTS

| | | | |
|---|---|---|---|
| 3,536,809 A | 10/1970 | Applezweig | 424/435 |
| 3,598,123 A | 8/1971 | Zaffaroni | 424/435 |
| 3,845,770 A | 11/1974 | Theeuwes | 424/427 |
| 3,916,899 A | 11/1975 | Theeuwes | 424/427 |
| 4,008,719 A | 2/1977 | Theeuwes et al. | 424/427 |
| 4,876,276 A | 10/1989 | Machoulam et al. | 514/454 |
| 4,880,830 A | 11/1989 | Rhodes | 424/470 |
| 4,973,603 A | 11/1990 | Burnstein | A61K 31/35 |
| 5,338,753 A | 8/1994 | Burstein et al. | 514/454 |
| 6,162,829 A | 12/2000 | Burstein | 514/570 |
| 6,355,650 B1 | 3/2002 | Burstein | 514/290 |
| 6,448,288 B1 | 9/2002 | Burstein et al. | 514/454 |

(Continued)

OTHER PUBLICATIONS

Russo, Future of Cannabis and Cannabinoids in Therapeutics. Journal of Canabis Therapeutics: The Official Journal of International Association for Cannabis. (2003);3(4):163.*

(Continued)

*Primary Examiner* — Savitha Rao
(74) *Attorney, Agent, or Firm* — Medlen & Carroll, LLP (57) ABSTRACT

The present invention relates to non-psychoactive derivatives of tetrahydrocannabinol, which are useful in treating interstitial cystitis and relieving symptoms thereof. The invention uses (6aR,10aR)-Δ⁸-tetrahydrocannabinol-11-oic acids (hereinafter referred to as (6aR,10aR)-Δ⁸-THC-11-oic acid), as well as pharmaceutical compositions containing the (6aR, 10aR)-Δ⁸-THC-11-oic acids, for treatment of interstitial cystitis in a mammal. The invention further covers methods of formulating and administering the compounds and pharmaceutical compositions as therapeutic agents in the treatment of interstitial cystitis, with particularly preferred administration routes being oral and via intravesicular instillation.

7 Claims, 9 Drawing Sheets

(56) References Cited

U.S. PATENT DOCUMENTS

| | | | |
|---|---|---|---|
| 2004/0048910 A1* | 3/2004 | Bove et al. | 514/381 |
| 2004/0054007 A1 | 3/2004 | Burstein et al. | 514/568 |
| 2004/0225011 A1 | 11/2004 | Burstein et al. | 514/454 |
| 2006/0128794 A1 | 6/2006 | Sandage | 514/454 |
| 2008/0097195 A1 | 4/2008 | Urquhart | 600/429 |
| 2008/0182892 A1 | 7/2008 | Sandage | 514/454 |

OTHER PUBLICATIONS

Morissette et al. Advanced Drug Delivery Reviews 2004, 56, 275-300.*

Vippagunta, Sudha R. "Crystalline Solids." Advanced Drug Delivery Reviews 48(2001): 3-26.*

Provisional U.S. Appl. No. 60/625,005, filed Dec. 13, 2004.

Provisional U.S. Appl. No. 60/658,578, filed Mar. 7, 2005.

Corey, E. J. and Samuelsson, B. (1984) One-step conversion of primary alcohols in the carbohydrate series to the corresponding carboxylic tert-butyl esters, *The Journal of Organic Chemistry* 49(24), 4735-4735.

Corey, E. J. and Venkateswarlu, A. (1972) Protection of hydroxyl groups as tert-butyldimethylsilyl derivatives, *J. Am. Chem. Soc.* 94(17), 6190-6191.

Mechoulam, R. et al. (1990) Synthesis of the individual, pharmacologically distinct, enantiomers of a tetrahydrocannabinol derivative, *Tetrahedron: Asymmetry* 1(5), 315-318.

Pellegata, R. et al. (1985) An Improved Procedure for the Synthesis of Oleuropeic Acid. I, *Synth. Commun.* 15(2), 165-170.

Daly DM, Collins VM, Chapple CR, Grundy D., The afferent system and its role in lower urinary tract dysfunction. Curr Opin Urol. Jul. 2011;21(4):268-74. Review.

Poonia MK, Kaur G, Chintamaneni M, Changela I., New insights into molecular targets for urinary incontinence. Indian J Pharmacol. Oct. 2010;42(5):261-6.

Mukerji G, Yiangou Y, Agarwal SK, Anand P., Increased cannabinoid receptor 1-immunoreactive nerve fibers in overactive and painful bladder disorders and their correlation with symptoms. Urology. Jun. 2010;75(6):1514.e15-20. Epub Mar. 25, 2010.

Sanchez Freire V, Burkhard FC, Kessler TM, Kuhn A, Draeger A, Monastyrskaya K., MicroRNAs may mediate the down-regulation of neurokinin-1 receptor in chronic bladder pain syndrome. Am J Pathol. Jan. 2010;176(1):288-303. Epub Dec. 11, 2009.

Tyagi V, Philips BJ, Su R, Smaldone MC, Erickson VL, Chancellor MB, Yoshimura N, Tyagi P., Differential expression of functional cannabinoid receptors in human bladder detrusor and urothelium. J Urol. Apr. 18, 2009, 1(4):1932-8. Epub Feb. 23, 2009.

Merriam FV, Wang ZY, Guerios SD, Bjorling DE. , Cannabinoid receptor 2 is increased in acutely and chronically inflamed bladder of rats. Neurosci Lett. Nov. 7, 2008;445(1):130-4. Epub Aug. 31, 2008.

Hayn MH, Ballesteros I, de Miguel F, Coyle CH, Tyagi S, Yoshimura N, Chancellor MB, Tyagi P , Functional and immunohistochemical characterization of CB1 and CB2 receptors in rat bladder. Urology. Nov. 2008;72(5):1174-8. Epub May 12, 2008.

Wiley JL , Ajulemic acid. IDrugs. Dec. 2005;8(12):1002-11. Review.

Dinis P, Charrua A, Avelino A, Yaqoob M, Bevan S, Nagy I, Cruz F. , Anandamide-evoked activation of vanilloid receptor 1 contributes to the development of bladder hyperreflexia and nociceptive transmission to spinal dorsal horn neurons in cystitis. J Neurosci. Dec. 15, 2004;24(50):11253-63.

Krenn H, Daha LK, Oczenski W, Fitzgerald RD , A case of cannabinoid rotation in a young woman with chronic cystitis. J Pain Symptom Manage. Jan. 2003;25(1):3-4. No abstract available.

Jaggar SI, Hasnie FS, Sellaturay S, Rice AS., The anti-hyperalgesic actions of the cannabinoid anandamide and the putative CB2 receptor agonist palmitoylethanolamide in visceral and somatic inflammatory pain. Pain. May 1998;76(1-2):189-99.

* cited by examiner

SUMMARY

| ICI | number | control (min) | AA 0.25% (min) |
|---|---|---|---|
| cremophor | 6 | 12.8 ± 1.6 | 5.11 ± 0.6** |
| 1 mg/kg | 5 | 13.7 ± 1.7 | 6.17 ± 1.3** |
| 3 mg/kg | 5 | 12.2 ± 2.9 | 5.18 ± 1.2 |
| 10 mg/kg | 6 | 11.8 ± 1.6 | 13.22 ± 2.7 |

| MVP | number | control (min) | AA 0.25% (min) |
|---|---|---|---|
| cremophor | 6 | 40.1 ± 4.5 | 43.2 ± 5.5 |
| 1 mg/kg | 5 | 37.6 ± 0.6 | 41.4 ± 1.3* |
| 3 mg/kg | 5 | 36.4 ± 2.4 | 43.5 ± 3.9 |
| 10 mg/kg | 6 | 32.5 ± 1.5 | 38.0 ± 4.0 |

| PT | number | control (min) | AA 0.25% (min) |
|---|---|---|---|
| cremophor | 6 | 7.5 ± 0.9 | 6.4 ± 0.8 |
| 1 mg/kg | 5 | 9.4 ± 0.7 | 6.9 ± 0.5* |
| 3 mg/kg | 5 | 8.7 ± 0.5 | 8.1 ± 0.4 |
| 10 mg/kg | 6 | 7.8 ± 0.7 | 9.6 ± 0.7 |

| BP | number | control (min) | AA 0.25% (min) |
|---|---|---|---|
| cremophor | 6 | 3.3 ± 0.6 | 3.7 ± 0.6* |
| 1 mg/kg | 5 | 3.5 ± 0.4 | 3.9 ± 0.6 |
| 3 mg/kg | 5 | 4.0 ± 0.3 | 4.9 ± 0.3 |
| 10 mg/kg | 6 | 3.6 ± 0.5 | 4.6 ± 0.6 |

**$P<0.01$, *$P<0.05$, PAIRED T-TEST

% OF CONTROL

| | ICI (%) | MVP (%) | PT (%) | BP (%) |
|---|---|---|---|---|
| cremophor | 42.9 ± 6.0 | 107.2 ± 4.0 | 87.1 ± 6.7 | 120.8 ± 10.8 |
| 1 mg/kg | 45.2 ± 7.6 | 110.0 ± 2.6 | 74.6 ± 6.8 | 111.2 ± 9.8 |
| 3 mg/kg | 51.1 ± 18.5 | 119.1 ± 7.0 | 94.1 ± 4.2 | 125.4 ± 12.4 |
| 10 mg/kg | 112.4 ± 13.0* | 116.5 ± 9.9 | 127.2 ± 12.6* | 131.1 ± 13.5 |

*$P<0.05$, (ONE-WAY ANOVA)

SUMMARY

| | CONTROL | VEHICLE | | CONTROL | 10mg/kg |
|---|---|---|---|---|---|
| ICI (min) | 3.95 ± 0.82 | 3.89 ± 0.72 | ICI (min) | 3.65 ± 0.52 | 5.14 ± 0.77* |
| MVP (cmH2O) | 52.67 ± 2.60 | 50.67 ± 2.17 | MVP (cmH2O) | 47.57 ± 2.90 | 42.69 ± 2.35 |
| PT (cmH2O) | 21.52 ± 2.84 | 21.64 ± 2.68 | PT (cmH2O) | 18.37 ± 1.41 | 17.7 ± 1.16 |
| BP (cmH2O) | 14.40 ± 2.01 | 13.80 ± 1.71 | BP (cmH2O) | 12.73 ± 1.17 | 11.44 ± 1.07* |

CYP treatment induced bladder overactivity and high compliance, which are blocked by IP-751 at a dose of 10 mg/kg

TREATMENT OF INTERSTITIAL CYSTITIS USING (6AR, 10AR)-Δ⁸-TETRAHYDROCANNABINOL-11-OIC ACIDS

CROSS REFERENCE TO RELATED APPLICATIONS

This application is a continuation of U.S. Ser. No. 12/070,342, (now abandoned) filed Feb. 15, 2008, which is a continuation of Ser. No. 11/299,688, (now abandoned) filed Dec. 13, 2005, which claims the benefit of prior U.S. provisional application 60/658,578, filed Mar. 7, 2005, and prior U.S. provisional application 60/625,005, filed Dec. 13, 2004, the contents of which are herein incorporated by reference.

FIELD OF THE INVENTION

The present invention relates to the treatment of interstitial cystitis using non-psychoactive derivatives of tetrahydrocannabinol, which exhibit anti-inflammatory and analgesic properties. In particular, the present invention further relates to the use of (6aR,10aR)-Δ⁸-tetrahydrocannabinol-11-oic acids, and pharmaceutical compositions comprising therapeutically effective amounts of the acids, for the treatment of interstitial cystitis.

BACKGROUND OF THE INVENTION

THC Derivatives

Δ⁹-Tetrahydrocannabinol [THC], depicted below as Formula I under alternate numbering systems, is the major psychoactive constituent of marijuana.

Δ¹-THC

Δ⁹-RHC

In addition to mood-altering effects, THC has been reported to exhibit other activities, some of which may have therapeutic value. The potential therapeutic value of THC has led to a search for related compounds which, while devoid of psychoactive effects, retain the activities of potential medicinal value.

Previous work with Δ⁸-tetrahydrocannabinol [6aR,7,10,10aR-tetrahydro-6,6,9-trimethyl-3-pentyl-6H-dibenzo[b,d]pyran-1-ol, hereinafter referred to as Δ⁸-THC], which is depicted below in Formula II, has indicated that certain derivatives of this compound may prove clinically useful.

Formula II

The 11-carboxy derivative of Δ⁸-THC [Δ⁸-THC-11-oic acid] has been reported to be a non-psychoactive, potent antagonist to endogenous platelet activating factor and, thus, a useful treatment for PAF-induced disorders, such as asthma, systemic anaphylaxis, and septic shock. (See U.S. Pat. No. 4,973,603, incorporated herein by reference.) Another derivative, (3S,4S)-11-hydroxy-Δ⁸-THC-1',1'dimethylheptyl, essentially free of the (3R,4R) form, has been reported to possess analgesic and anti-emetic activities. (See U.S. Pat. No. 4,876,276, also incorporated herein by reference.)

Interstitial Cystitis

Interstitial cystitis (IC) is a chronic pelvic pain disorder that results in recurring discomfort or pain in the bladder and the surrounding pelvic region. The symptoms of IC vary form case to case and even in the same individual. Patients may experience mild discomfort, pressure, tenderness, or intense pain in the bladder and pelvic area. Symptoms may include an urgent need to urinate and/or frequent need to urinate. The pain may change in intensity as the bladder fills with urine or as it empties.

In IC, the bladder wall may be irritated and become scarred or stiff. Glomerulations (pinpoint bleeding caused by recurrent irritation) may appear on the bladder wall. Some people with IC find that their bladders cannot hold much urine, which increases the frequency of urination. Also, people with IC often experience pain during sexual intercourse.

Because IC symptoms and severity vary greatly, most researchers believe that it encompasses not one, but several, diseases. In the past, cases were mainly categorized as ulcerative IC or nonulcerative IC, based on whether ulcers had formed on the bladder wall. Even today, it is easier to define IC by what it isn't than by what it is, and to reach a diagnosis of IC, the physician must first rule out bacterial cystitis—the most common urinary tract infection—whose symptoms it most closely resembles. Bladder cancer, kidney stones, vaginitis, endometriosis, sexually transmitted diseases, tuberculosis, and radiation cystitis, as well as prostate infections in men, are some other conditions that must be considered. Thus, IC is a diagnosis of exclusion.

Although some of the symptoms of IC resemble those of a bacterial infection, medical tests reveal no organisms in the urine of patients with IC. Furthermore, patients with IC do not respond to antibiotic therapy. Researchers are still working to understand the causes of IC and to find effective treatments. Some have suggested it may be an autoimmune disorder of the bladder's connective tissue, in which the body's defense mechanisms against invading bacteria turn suddenly against healthy tissue. In some patients, special white blood cells called mast cells, which are associated with inflammation, are found within the bladder's mucous lining. It has also been theorized that the disorder may be an allergic reaction, because many patients have a history of allergies. Some scientists have suggested that certain substances in urine may be irritating to people with IC, but no substance unique to people with IC has as yet been isolated.

Another theory is that a bacterium may be present in bladder cells but not detectable through routine urine tests. Researchers are also beginning to explore the possibility that heredity may play a part in some forms of IC, but no gene has yet been implicated. One theory holds that the inner lining of the bladder (the glycosaminoglycan or GAG layer) that protects the bladder wall from toxic effects of urine may be "leaky," allowing substances in the urine to penetrate the bladder wall and trigger IC symptoms. A recent study found that 70 percent of IC patients they examined had a "leaky" bladder lining.

There is no cure for IC, and current therapies are aimed at trying to relieve the symptoms, which vary from person to person. People may have flare-ups and remissions, and different patients respond to different treatments. A particular type of therapy may work for a while and then lose its effectiveness. Sometimes, stress or a change of diet triggers symptoms. Occasionally, IC goes into remission spontaneously. Even when symptoms disappear, they may return after days, weeks, months, or years.

Factors that influence the treatment options available typically include whether bladder capacity under anesthesia is great or small, and whether mast cells are present in the tissue of the bladder wall, which may be a sign of an allergic or autoimmune reaction. In some cases, the success or failure of a treatment helps characterize the type of IC. Some current treatments for IC include bladder distention, administration of pharmaceutical compositions by bladder instillation (also known as intravesicular instillation (IVI)), oral administration of pharmaceutical compositions, and transcutaneous electrical nerve stimulation. These treatment options will be described in greater detail below.

Bladder distention is often performed to diagnose IC, but because many patients have noted an improvement in symptoms after the procedure, it is often thought of as one of the first treatment attempts. Researchers are not sure why distention helps, but some believe that it may increase capacity and interfere with pain signals transmitted by nerves in the bladder. Symptoms may temporarily worsen 24 to 48 hours after distention, but should return to predistention levels or improve after 2 to 4 weeks.

During bladder instillation or intravesicular instillation (IVI), which may also be called a bladder wash or bath, the bladder is filled with a solution that is held for varying periods of time, averaging 10 to 15 minutes, before being emptied. IVI is typically performed using dimethyl sulfoxide (DMSO, RIMSO-50). DMSO IVI treatment involves guiding a catheter up the urethra into the bladder. A measured amount of DMSO is passed through the catheter into the bladder, where it is retained for about 15 minutes before being expelled. Treatments are usually given every week or two for 6 to 8 weeks and repeated as needed. Doctors think IVI administration of DMSO works in several ways. Because it passes into the bladder wall, it may reach tissue more effectively to reduce inflammation and block pain. It may also prevent muscle contractions that cause pain, frequency, and urgency.

Pentosan polysulfate sodium (Elmiron®) was the first oral drug developed for IC to have been approved by the FDA. In clinical trials, the drug improved symptoms, but its method of action is unknown. One theory is that it may repair defects that might have developed in the lining of the bladder. The FDA-recommended oral dosage of Elmiron is 100 mg, three times a day. Patients may not feel relief from IC pain for the first 2 to 4 months. A decrease in urinary frequency may take up to 6 months to achieve.

Other oral medications such as aspirin and ibuprofen may be used as a first line of defense against mild discomfort. Doctors may recommend other drugs to relieve pain. Some patients may experience improvement in their urinary symptoms by taking antidepressants or antihistamines. Antidepressants help reduce pain and may also help patients deal with the psychological stress that accompanies living with chronic pain. In patients with severe pain, narcotic analgesics such as acetaminophen with codeine or longer acting narcotics may be necessary.

Transcutaneous electrical nerve stimulation (TENS) involves having mild electric pulses enter the body for minutes to hours two or more times a day, either through wires placed on the lower back or just above the pubic area, between the navel and the pubic hair, or through special devices inserted into the vagina in women or into the rectum in men. Although scientists do not know exactly how TENS relieves IC pain, it has been suggested that the electrical pulses may increase blood flow to the bladder, strengthen pelvic muscles that help control the bladder, or trigger the release of substances that block pain.

None of the currently used treatments for IC is capable of fully relieving the symptoms of IC. Patients frequently combine different treatments in an attempt to address all of their IC symptoms. Further, patients usually cannot achieve long term relief using any of these treatments, and once a particular treatment loses its effectiveness, the patient must introduce a new treatment in its place. Clearly, although numerous treatments have been developed in an attempt to control the symptoms of IC, there is still a great need in the art for effective treatments for IC.

DESCRIPTION OF RELATED ART

U.S. Pat. No. 5,338,753 discloses (3R,4R)-$\Delta^6$-THC-7-oic acids (which correspond to (6aR,10aR)-$\Delta^8$-THC-11-oic acids, but were named using an alternative numbering system) that are useful as anti-inflammatory agents and analgesics, as well as methods of synthesizing them, but does not disclose compositions or methods for treating patients suffering from IC.

U.S. Pat. Nos. 6,162,829 and 6,355,650 disclose derivatives of (6aR,10aR)-$\Delta^8$-THC-11-oic acids that are also useful as anti-inflammatory agents and analgesics, and methods of synthesizing them. They do not disclose compositions or methods for treating patients suffering from IC.

U.S. Pat. No. 6,448,288 discloses the use of $\Delta^8$-THC-11-oic acids to decrease cell proliferation, but fails to disclose compositions or methods for treating patients suffering from IC.

U.S. Published Application No. 2004/0054007 discloses methods for decreasing cell proliferation using (6aR,10aR)-$\Delta^8$-THC-11-oic acid, but it also fails to disclose compositions or methods for treating patients suffering from IC.

U.S. Published Application No. 2004/0225011 discloses methods of using cannabinoid compounds that are derivatives of THC to decrease cell proliferation, and does not disclose compositions or methods for treating patients suffering from IC.

The disclosures of each of these patents and published applications are incorporated herein by reference in their entirety.

It is desired, however, to provide a method of treating, alleviating, and/or relieving symptoms associated with IC by use of the $\Delta^8$-THC-11-oic acid derivatives, such as those described above, as well as pharmaceutical compositions suitable for such use. The present invention may control the symptoms and improve the quality of life for patients suffering from IC and may also reduce the urgency and frequency associated with urination.

SUMMARY OF THE INVENTION

It is an advantage of the present invention to provide compositions and methods for treating a patient suffering from interstitial cystitis, whereby the (6aR,10aR)-$\Delta$8-THC-1'-oic acids according to the present invention are advantageously administered to said patient.

According to a first aspect of the present invention, unique methods are provided for the treatment of interstitial cystitis in a mammal using a compound having Formula II Formula II wherein $R^1$ is hydrogen, —$COCH_3$ or —$COCH_2CH_3$; and $R^2$ is a branched $C_5$-$C_{12}$ alkyl compound which may optionally have a terminal aromatic ring, or optionally a branched —$OCHCH_3(CH_2)_m$ alkyl compound which may have a terminal aromatic ring, wherein m is 0 to 7. The method comprises the steps of identifying a mammal suffering from or suspected of suffering from interstitial cystitis; and administering to the mammal an effective amount of the compound of formula II, or a pharmaceutically acceptable salt, ester, or solvate thereof.

According to a second aspect of the present invention, unique compositions and methods are provided for a pharmaceutical composition for use in treating interstitial cystitis in a mammal, particularly humans, including a therapeutically effective amount of a compound having Formula II Formula II wherein $R^1$ is hydrogen, —$COCH_3$ or —$COCH_2CH_3$; and $R^2$ is a branched $C_5$-$C_{12}$ alkyl compound, which may optionally have a terminal aromatic ring, or optionally a branched —$OCHCH_3(CH_2)_m$ alkyl compound, which may have a terminal aromatic ring, wherein m is 0 to 7, or a pharmaceutically acceptable salt, ester or solvate thereof. The pharmaceutical composition may optionally include a therapeutically effective amount of one or more compounds selected from the group consisting of sodium pentosanpolysulfate, antihistamines, antidepressants, imipramine, antispasmodics, urinary anesthetics, and capsaicin. The pharmaceutical composition may also optionally include a therapeutically effective amount of an anticholinergic agent selected from the group consisting of anisotropine, aprophen, artane, atropine, belladonna, benactyzine, benztropine, clidinium, dicyclomine, glycopyrrolate, homatropine, hyoscyamine, isopropamide, mepenzolate, methantheline, methscopolamine, oxybutynin, oxyphencyclimine, propantheline, scopolamine, terodiline, tridihexethyl, trihexyphenidyl, and trospium.

According to a third aspect of the present invention, unique compositions and methods are provided for pharmaceutical composition for use in treating interstitial cystitis in a mammal, including an effective amount of a compound having Formula III or a pharmaceutically acceptable salt, ester or solvate thereof.

In another aspect of the invention, subjects suffering from or suspected of suffering from IC are treated by administering an effective amount of at least one compound selected from the compound of Formula II or III, or a pharmaceutically acceptable salt, ester, or solvate thereof.

BRIEF DESCRIPTION OF THE DRAWINGS

Exemplary embodiments of the presently preferred features of the present invention will now be described with reference to the accompanying drawings.

DETAILED DESCRIPTION OF THE PRESENTLY PREFERRED EMBODIMENTS

Introduction

The present invention relates to (6aR,10aR)-$\Delta^8$-THC-11-oic acids, pharmaceutical compositions comprising therapeutically effective amounts of these compounds, and methods of treating IC in a mammal by administering such compounds or pharmaceutical compositions. The THC derivatives of the present invention have reduced or no psychoactivity and do not bind to the CB1 receptor. A particularly preferred

Δ⁸-THC-11-oic acid analog in accordance with the present invention is 1',1'-dimethylheptyl-Δ⁸-THC-11-oic acid (also known as CT3 or ajulemic acid), shown below in Formula III, although use of other THC derivatives in the treatment of IC is specifically envisioned by the present invention.

The Compositions of the Preferred Embodiments

The present invention relates to compositions and pharmaceuticals useful in relieving symptoms of IC, which comprise Δ⁸-THC-11-oic acids and derivatives and analogs thereof, as depicted below in Formula II:

Formula II wherein $R^1$ is hydrogen, —COCH₃ or —COCH₂CH₃; $R^2$ is a branched $C_5$-$C_{12}$ alkyl compound, which may optionally have a terminal aromatic ring, or optionally a branched —OCHCH₃(CH₂)$_m$ alkyl compound, which may have a terminal aromatic ring, wherein m is 0 to 7.

Particularly preferred compounds are obtained when $R^1$ is hydrogen, and $R^2$ is 1',1'-dimethylheptyl (IP-751). Thus, in this preferred form, the compounds have the formula shown in Formula III below:

The preferred compounds are also similarly preferred when used in pharmaceutical compositions and for methods of treating IC by administration of the compounds or pharmaceutical compositions according to the invention.

The phrase "therapeutically effective amount" means that amount of the pharmaceutical composition that provides a therapeutic benefit in the treatment, prevention, or management of interstitial cystitis.

Dosage amounts for the (6aR,10aR)-Δ⁸-THC-11-oic acids according to the present invention, when administered orally for the relief of symptoms of IC, are generally between about 1 mg and about 200 mg, preferably between about 10 mg and about 100 mg per day, and more preferably between about 20 mg and about 60 mg per day, administered about 2 to about 4 times daily. As would be understood by one skilled in the art, the dose, and dose frequency, will vary according to the patient's age, body weight, and therapeutic response, as well as the severity of the condition.

The orally administered compounds and pharmaceutical compositions according to the present invention may be optionally administered in conjunction with other existing oral treatments for IC, including, but not limited to, sodium pentosanpolysulfate (Elmiron®), preferably administered as about 100 mg three times a day; antihistamines such as hydroxizine (Atarax® Vistaril®); antidepressants (for their direct effect on bladder pain fibers) such as amitriptyline HCL (Elavil®, Triavil®), preferably administered as from about 25 mg to about 75 mg daily, or doxepin HCL (Sinequan®), preferably administered as about 75 mg at bedtime; imipramine (Trazodone®), preferably administered as about 25 mg three times a day; antispasmodics (Anaspaz®, Cystospaz®, Ditropan®, Levsin®, Levsinex®, Urispas®, Urised®); urinary anesthetics such as phenazopyridine (Pyridium®, Uristat®); and capsaicin. Preferably, they are administered in a manner consistent with their present use in the treatment of IC.

The orally administered compounds and pharmaceutical compositions according to the present invention may be optionally administered in conjunction with existing treatments for IC that are administered via IVI.

The compounds and pharmaceutical compositions according to the present invention may also be beneficially administered as formulations for use in bladder instillation or intravesicular instillation (IVI).

Dosage amounts for the (6aR,10aR)-Δ⁸-THC-11-oic acids according to the present invention, when administered via IVI, are generally between about 12.5 and about 3500 ng/ml exposure within the bladder per administration, preferably between about 20 ng/ml exposure to about 2,000 ng/ml exposure within the bladder per administration. More preferably, the amount of exposure of the patient to the compounds of interest within the bladder per administration ranges from about 50 ng/ml to less than about 1,000 ng/ml. Depending on the amount of urine in the bladder, and the instilled volume (usually approximately 25 ml), the dose would be less than about 1 mcg to about 100 mcg per administration, preferably less than about 10 mcg to about 50 mcg, more preferably less than about 20 mcg to about 40 mcg, administered twice, once or fewer times daily. As would be understood by one skilled in the art, the dose, and dose frequency, will vary according to the patient's age, body weight, and therapeutic response, as well as the severity of the condition.

The compounds and pharmaceutical compositions according to the present invention may be administered via IVI, optionally in conjunction with other existing IVI treatments for the side effects of IC, including, but not limited to, dimethyl sulfoxide (DMSO), heparin, hyaluronic acid, Cystitat, silver nitrate, chlorpactin, and Bacillus Calmette Guerin (BCG). Other compositions suitable for administration via IVI may also be combined with the compositions and pharmaceuticals of the present invention. Preferably, they are administered in a manner consistent with their present use in the treatment of IC.

The compounds and pharmaceutical compositions according to the present invention may be administered via IVI, optionally in conjunction with other existing orally administered treatments for the side effects of IC.

According to a particularly preferred aspect of the present invention, the compounds and pharmaceutical compositions may optionally be administered in conjunction with an anticholinergic agent. The anticholinergic agent is preferably administered orally or via IVI, although other routes of administration are contemplated in accordance with the present invention. Such anticholinergic agents may be selected from anisotropine, aprophen, artane, atropine; belladonna, benactyzine, benztropine, clidinium, dicyclomine, glycopyrrolate, homatropine, hyoscyamine, isopropamide, mepenzolate, methantheline, methscopolamine, oxybutynin, oxyphencyclimine, propantheline, scopolamine, terodiline, tridihexethyl, trihexyphenidyl, and trospium. Use of other compounds including an anticholinergic action is specifically envisioned by the present invention. Preferably, the anticholinergic agents are administered in a manner consistent with their present use in the treatment of IC.

The pharmaceutical compositions of the present invention may include the active ingredients described above, and may also contain pharmaceutically acceptable carriers, excipients and the like, and optionally, other therapeutic ingredients. In one embodiment, for example, the drug may be suspended in a vegetable oil, such as olive oil or peanut oil, and, optionally encapsulated in a gelatin capsule. For human therapy, the compounds or pharmaceutical compositions are preferably administered orally, in the form of a gelatin capsule, or by IVI in the form of a suspension or solution.

The term "pharmaceutically acceptable salt" refers to a salt prepared from pharmaceutically acceptable non-toxic acids or bases including inorganic or organic acids. Examples of such inorganic acids are hydrochloric, hydrobromic, hydroiodic, sulfuric, and phosphoric. Appropriate organic acids may be selected, for example, from aliphatic, aromatic, carboxylic and sulfonic classes of organic acids, examples of which are formic, acetic, propionic, succinic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic, stearic, sulfanilic, algenic, and galacturonic. Examples of such inorganic bases, for potential salt formation With sulfate or phosphate compounds of the invention, include metallic salts made from aluminum, calcium, lithium, magnesium, potassium, sodium, and zinc. Appropriate organic bases may be selected, for example, from N,N-dibenzylethylenediamine, chloroprocaine, choline, diethanolamine, ethylenediamine, meglumaine (N-methylglucamine), and procaine. The compounds and pharmaceutical compositions of the present invention may be administered in the form of such pharmaceutically acceptable salts. The compounds of interest may also be administered in the form of esters, e.g., methyl, ethyl and the like. Solvates of the compounds of interest may also be useful, including hydrates and the like.

The compounds and pharmaceutical compositions of the present invention may also be included in formulations such as suspensions, solutions and elixirs; aerosols; or carriers such as starches, sugars, microcrystalline cellulose, diluents, granulating agents, lubricants, binders, disintegrating agents, and the like, in the case of oral solid preparations (such as powders, capsules, and tablets), with oral solid preparations being preferred over oral liquid preparations. The most preferred oral solid preparations are capsules.

Because of their ease of administration, tablets and capsules represent the most advantageous oral dosage unit form, in which case solid pharmaceutical carriers are employed. If desired, tablets may be coated by standard aqueous or nonaqueous techniques. Because of the benefits of IVI for relieving symptoms of IC, IVI formulations are another particularly preferred dosage form, in which case the compounds and pharmaceutical compositions of the present invention are provided dissolved or suspended in a pharmaceutically acceptable solvent or diluent.

In addition to the dosage forms set out above, the compounds and pharmaceuticals of the present invention may also be administered by controlled release means and/or delivery devices such as those described in U.S. Pat. Nos. 3,845,770; 3,916,899; 3,536,809; 3,598,123; and 4,008,719, the disclosures of which are hereby incorporated by reference.

The Methods of the Preferred Embodiments

The compounds and pharmaceutical compositions of the present invention can be used in methods of treating mammals suffering from IC, in both veterinary medicine and human therapy contexts. The method of administering the compounds and pharmaceutical compositions in the acute or chronic management of IC will vary with the severity of the condition and the route of administration. The dose, and perhaps the dose frequency, will also vary according to the age, body weight, and response of the individual patient. The actual preferred amounts of the active ingredients administered will vary with each case, according to the species of mammal, the nature and severity of affliction being treated, and the method of administration. In general, the compounds and pharmaceutical compositions of the present invention are periodically administered to an individual patient as necessary to improve symptoms associated with IC. The length of time during which the compounds and pharmaceutical compositions are administered and the total dosage will necessarily vary with each case, according to the nature and severity of the IC with which the patient is afflicted, and the physical condition of the subject.

The compounds and pharmaceutical compositions may be administered via any appropriate route, e.g. intravenously, intraarterially, topically, by injection, intraperitoneally, intrapleurally, orally, subcutaneously, intramuscularly, sublingually, intraepidermally, or rectally. The preferred methods of administration are orally and via IVI. The oral formulations may be solutions, suspensions, suppositories, tablets, granules, powders, capsules, ointments, or creams. The IVI formulations may be solutions or suspensions, including compositions comprising liposomes. In the preparation of the pharmaceuticals, a solvent (e.g., water or physiological saline), solubilizing agent (e.g., ethanol, Polysorbates, or Cremophor EL7), agent for making isotonicity, preservative, antioxidizing agent, excipient (e.g., lactose, starch, crystalline cellulose, mannitol, maltose, calcium hydrogen phosphate, light silicic acid anhydride, or calcium carbonate), binder (e.g., starch, polyvinylpyrrolidone, hydroxypropyl cellulose, ethyl cellulose, carboxy methyl cellulose, or gum arabic), lubricant (e.g., magnesium stearate, talc, or hardened oils), or stabilizer (e.g., lactose, mannitol, maltose, polysorbates, macrogols, or polyoxyethylene hardened castor oils) can be added. If necessary, glycerin, dimethylacetamide, 70% sodium lactate, a surfactant, or a basic substance such as sodium hydroxide, ethylenediamine, ethanolamine, sodium bicarbonate, arginine, meglumine, or trisaminomethane is added. Pharmaceutical preparations such as solutions, tablets granules or capsules can be formed with these components. Compositions for slow release of the compound can be formed as described in U.S. Pat. No. 4,880,830.

Generally, the oral administration methods and formulations of the present invention provide between about 1 mg and about 200 mg per day, preferably between about 10 mg and about 100 mg per day, and more preferably between about 20 mg and about 60 mg per day, administered about 2 to about 4 times daily, of the (6aR,10aR)—$\Delta^8$-THC-11-oic acids (i.e., excluding excipients, carriers, and any of the optional additional active ingredients described herein). If desired, the daily dose may include two or more unit doses, i.e., tablets, cachets or capsules, to be administered each day.

Dosage amounts for the IVI methods of administration and formulation of the present invention are generally between about 12.5 and about 3500 ng/ml exposure within the bladder per administration, preferably between about 20 ng/ml exposure to about 2,000 ng/ml exposure within the bladder per administration. More preferably, the amount of exposure of the patient to the compounds of interest within the bladder per administration ranges from about 50 ng/ml to less than about 1,000 ng/ml. Depending on the amount of urine in the bladder, and the instilled volume (usually approximately 25 ml), the dose would be less than about 1 mcg to about 100 mcg per administration, preferably less than about 10 mcg to about 50 mcg, more preferably less than about 20 mcg to about 40 mcg, administered twice, once or fewer times daily. As would be understood by one skilled in the art, the dose, and dose frequency, will vary according to the patient's age, body weight, and therapeutic response, as well as the severity of the condition.

It is further recommended that children, patients aged over 65 years, and those with impaired renal or hepatic function initially receive low doses, and that they then be titrated based on individual response(s) or blood level(s). It may be necessary to use dosages outside these ranges in some cases, as will be apparent to those of ordinary skill in the art. Further, it is noted that the clinician or treating physician will know how and when to interrupt, adjust, or terminate therapy in conjunction with individual patient response.

The methods of the present invention envision the optional inclusion of existing treatments for IC in conjunction with the methods of administration and formulation of compounds and pharmaceutical compositions comprising the (6aR, 10aR)-$\Delta^8$-THC-11-oic acids of the present invention.

Also envisioned are methods of administration and formulation that provide for the optional inclusion of anticholinergic agents with the administration and formulation of compounds and pharmaceutical compositions comprising the (6aR,10aR)-$\Delta^8$-THC-11-oic acids of the present invention.

According to an additional embodiment of the present invention, the methods of administration and formulation include the administration and formulation of compounds and pharmaceutical compositions comprising the (6aR, 10aR)-$\Delta^8$-THC-11-oic acids in accordance with the present invention, in conjunction with both anticholinergic agents and existing treatments for IC.

These methods of administration and formulation of the present invention are beneficially used to treat symptoms caused by IC. Preferably, the existing IC treatments and/or anticholinergic agents are formulated or co-administered with the (6aR,10aR)-$\Delta^8$-THC-11-oic acids in accordance with the present invention in a manner that is consistent with their present use in the treatment of IC.

The optional addition of existing treatments for IC to the methods of the present invention may include oral administration of sodium pentosanpolysulfate (Elmiron®), preferably administered as about 100 mg three times a day; antihistamines such as hydroxizine (Atarax® Vistaril®); antidepressants (for their direct effect on bladder pain fibers) such as amitriptyline HCL (Elavil®, Triavil®), preferably administered as from about 25 mg to about 75 mg daily, or doxepin HCL (Sinequan®), preferably administered as about 75 mg at bedtime; imipramine (Trazodone®), preferably administered as about 25 mg three times a day; antispasmodics (Anaspaz®, Cystospaz®, Ditropan®, Levsin®, Levsinex0, Urispas®, Urised®); urinary anesthetics such as phenazopyridine (Pyridium®, Uristat®); and capsaicin. Other IC treatments suitable for oral administration may also be combined with the compounds and pharmaceutical compositions of the present invention. Where appropriate, these oral IC treatments may be formulated as a single unit dose with the compounds and pharmaceutical compositions of the present invention. When such formulations are not possible or desirable, these oral IC treatments may be beneficially co-administered with the compounds and pharmaceutical compositions of the present invention.

The optional addition of existing IVI treatments for IC to the methods of the present invention may include administration of IVI formulations of dimethyl sulfoxide (DMSO), heparin, hyaluronic acid, Cystitat, silver nitrate, chlorpactin, and Bacillus Calmette Guerin (BCG). Other IC treatments suitable for administration via IVI may also be combined with the compounds and pharmaceutical compositions of the present invention. Other IC treatments suitable for oral administration may also be combined with the compounds and pharmaceutical compositions of the present invention. Where appropriate, these IVI formulated IC treatments may be formulated as a single solution or suspension with the compounds and pharmaceutical compositions of the present invention. When such formulations are not possible or desirable, these IVI formulated IC treatments may be beneficially co-administered with the compounds and pharmaceutical compositions of the present invention.

According to a particularly preferred aspect of the present invention, the oral and IVI administration and formulation methods of the present invention may optionally include providing an anticholinergic agent in the formulation, where feasible, or coadministering the anticholinergic agent with the compounds and pharmaceutical compositions of the present invention. Such anticholinergic agents may be selected from anisotropine, aprophen, artane, atropine, belladonna, benactyzine, benztropine, clidinium, dicyclomine, glycopyrrolate, homatropine, hyoscyamine, isopropamide, mepenzolate, methantheline, methscopolamine, oxybutynin, oxyphencyclimine, propantheline, scopolamine, terodiline, tridihexethyl, trihexyphenidyl, and trospium. Use of other compounds including an anticholinergic action is specifically envisioned by the present invention.

Pharmaceutical compositions for use in the methods of the present invention suitable for oral administration may be presented as discrete units such as capsules, cachets, or tablets, or aerosol sprays, each containing a predetermined amount of the active ingredient, as a powder or granules, as creams, pastes, gels, or ointments, or as a solution or a suspension in an aqueous liquid, a non-aqueous liquid, an oil-in-water emulsion, or a water-in-oil liquid emulsion. Formulations that include micelles are also contemplated. Such compositions may be prepared by any of the methods of pharmacy, but all methods include the step of bringing into association the carrier with the active ingredient which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or molding, optionally, with one or more accessory ingredients. Compressed tablets may be prepared by compressing in a suitable machine the active ingredient in a free-flowing form, such as powder or granules, optionally mixed with a binder (e.g., carboxymethylcellulose, gum arabic, gelatin), filler (e.g., lactose), adjuvant, flavoring agent, coloring agent, lubricant, inert diluent, coating material (e.g., wax or plasticizer), and a surface active or dispersing agent. Molded tablets may be made by molding, in a suitable machine, a mixture of the powdered compound moistened with an inert liquid diluent. Those skilled in the art will know, or will be able to ascertain with no more than routine experimentation, appropriate pharmacological carriers for said pharmaceutical compositions.

When the compositions and pharmaceuticals according to the present invention are administered using the IVI method, it is preferred that they be provided as dispersions, suspensions, or solutions.

The methods of the present invention may comprise administering to an afflicted individual a compound or pharmaceutical composition comprising an effective amount of the (6aR,10aR)-$\Delta^8$-THC-11-oic acids of the present invention for use in treating IC, where the compositions are provided in a pharmacologically acceptable carrier, for example, a gelatin capsule, or edible oil (e.g., a vegetable oil) for oral administration; or a pharmaceutical composition comprising an effective amount of the (6aR,10aR)-$\Delta^8$-THC-11-oic acids of the present invention, which may be optionally provided in liposomes and suspended in a sterile saline solution for IVI administration.

The methods of the present invention include the determination of optimum doses of the compounds and pharmaceutical compositions for treating IC symptoms, which may be determined in consideration of the results of animal experiments. More specific doses obviously vary depending on the administration method, the condition of the subject such as age, body weight, sex, sensitivity, food eaten, dosage intervals, medicines administered in combination, and the seriousness and degree of the IC. The optimal dose and the administration frequency under a given condition must be determined by the appropriate dosage test of a medical specialist based on the aforementioned guidelines, and does not constitute undue experimentation for one skilled in the art.

EXAMPLES

The invention is further defined by reference to the following examples describing in detail the preparation of the compound and the compositions used in the methods for treating IC according to the present invention, as well as their utility. The examples are representative, and they should not be construed to limit the scope of the invention.

a. Preparation of Derivatives

Figure 1:
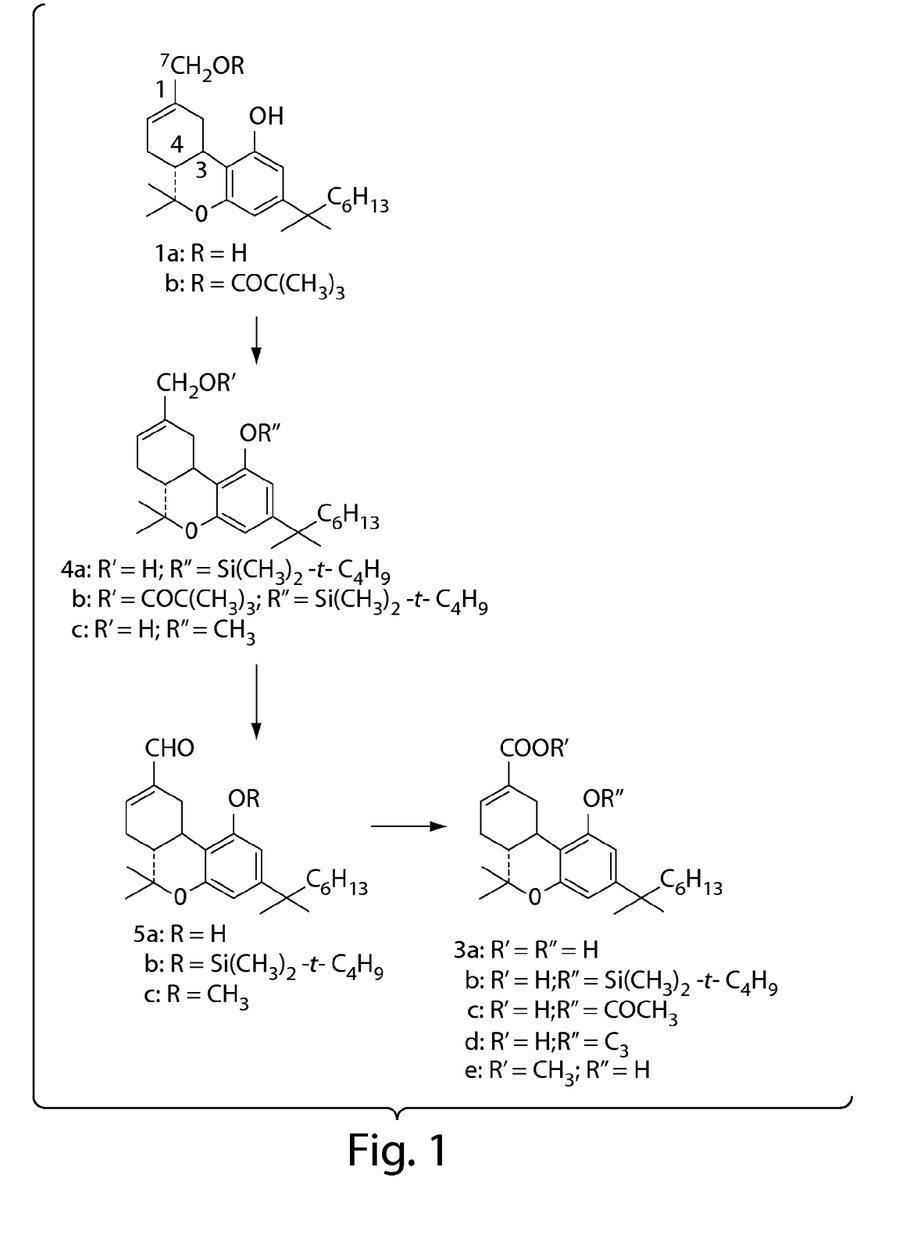
FIG. 1 is a synthetic scheme for the (6aR,10aR)-$\Delta^8$-THC-11-oic acids of the present invention.
Figure 2:
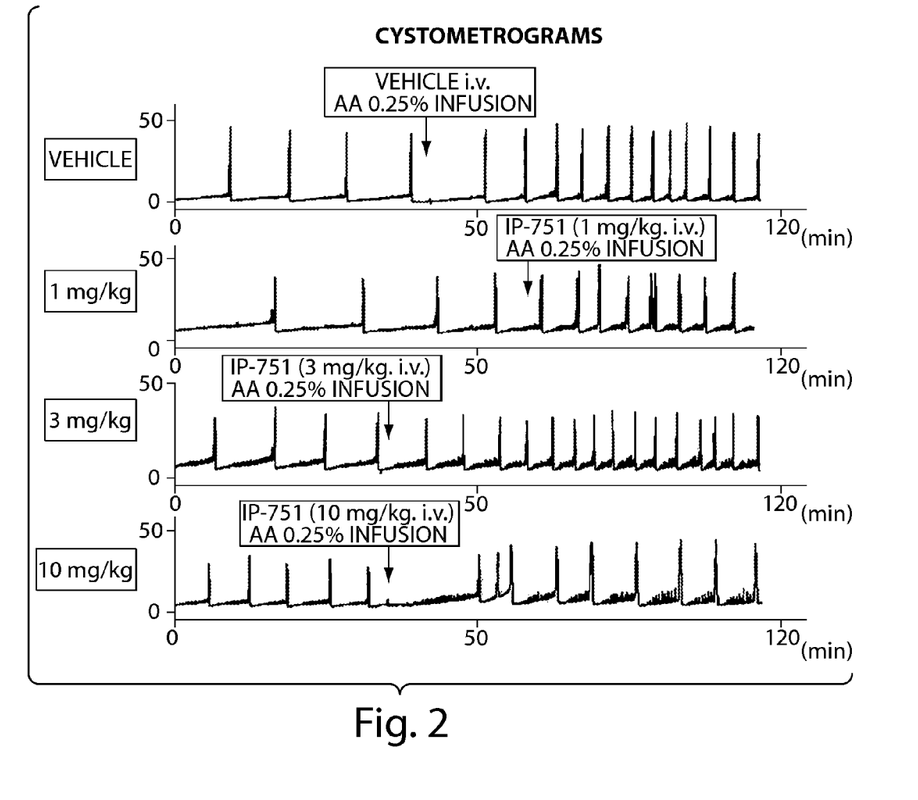
FIG. 2 shows cystometrograms relating to Example i.
Figure 3:
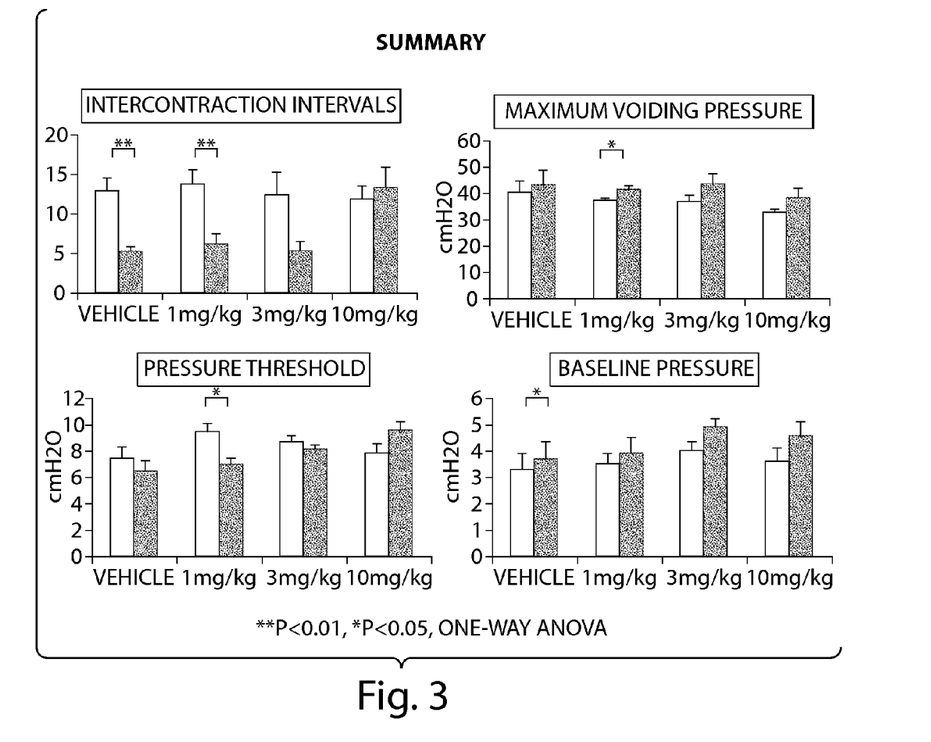
FIG. 3 is a summary of results of Example i.
Figure 4:
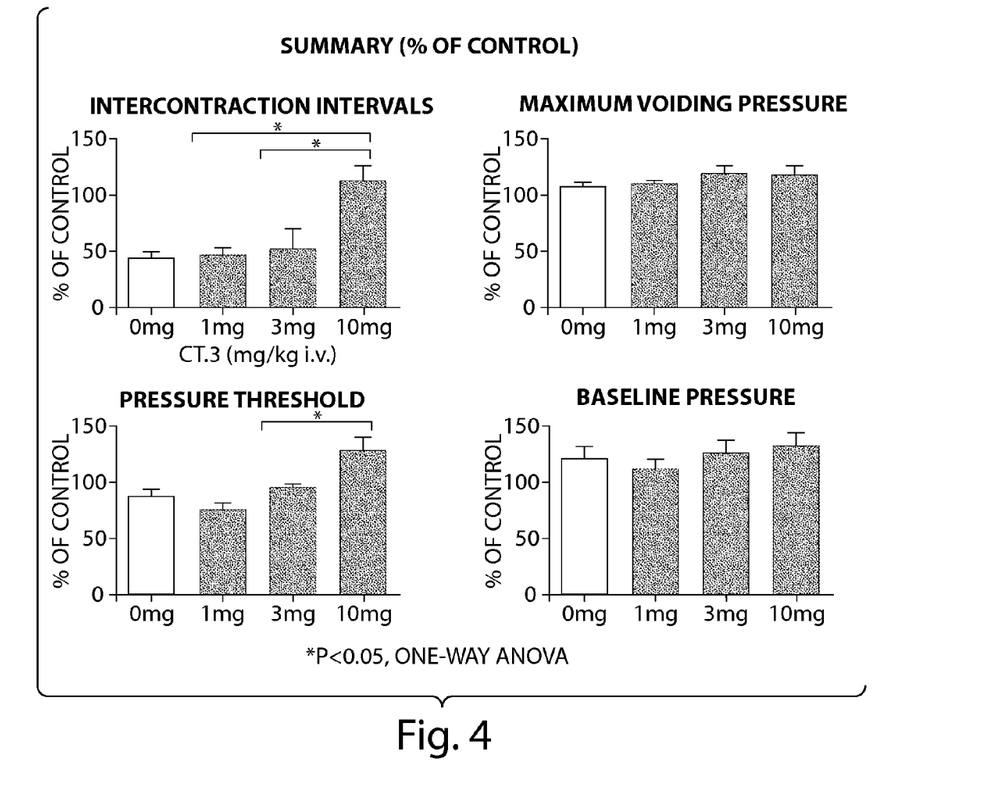
FIG. 4 is a summary of results of Example i, expressed as a percent of control.
Figure 5:
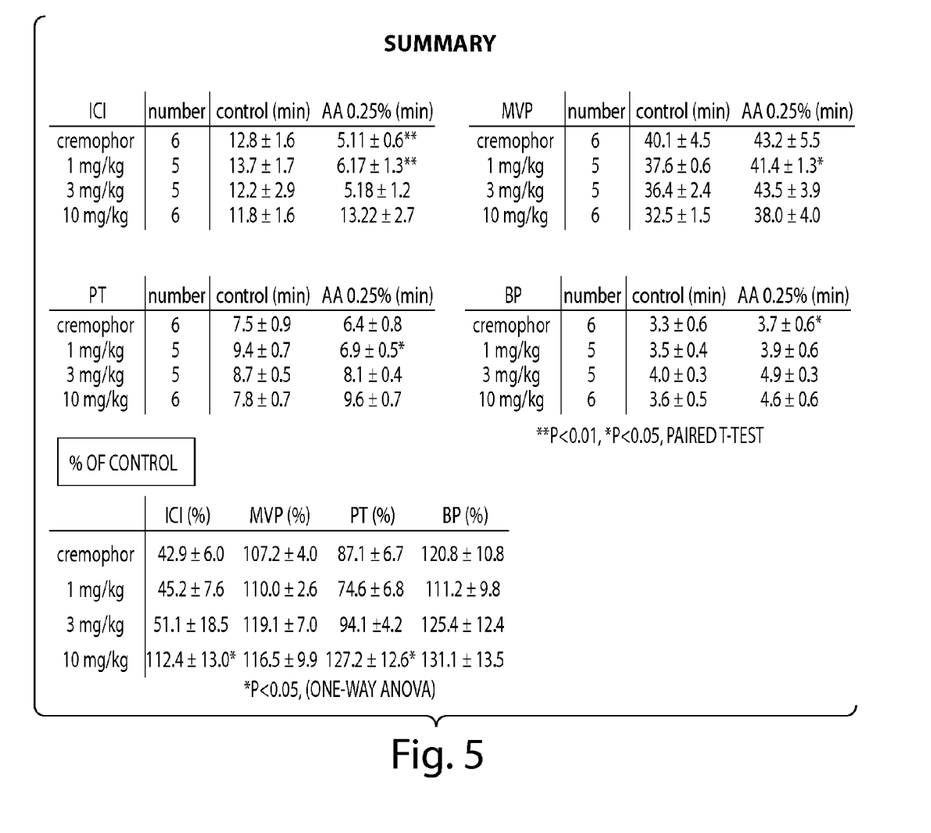
FIG. 5 is a summary of the numerical results of Example i.

The compounds of the present invention may be prepared according to the synthetic scheme depicted in FIG. 1.

In general, melting points were taken in glass capillary tubes with a Thomas-Hoover Uni-Melt apparatus. Infrared spectra were recorded on a JASCO A-200 spectrophotometer. Rotations were determined on a Perkin-Elmer Model 141 polarimeter in chloroform. Chromatographic separations were performed on silica gel columns (Woelm TSC silica, for dry chromatography, activity III/30 mm, No. 04530). The high-resolution mass spectrometry (HRMS was performed on a Varian 711 instrument.

b. Synthesis of Compound 4a

In general, this esterification follows the procedure of Corey and Venkateswarlu (Corey E. J. and Venkateswarlu A. "Protection of Hydroxyl Groups as Tert-Butyldimethylsilyl Derivatives." J. Am. Chem. Soc. 94:6190 (1972). Compound 1b (2.9 g, 6.17 mmol), $[\forall]_D$ 1152.60 (c 17.2 m/mL, CHCl$_3$), prepared according to Mechoulam et al. (Mechoulam R. et al. "Synthesis of the Individual, Pharmacologically Distinct, Enantiomers of a Tetrahydrocannabinol Derivative." Tetrahydron: Asymmetry 1:315 (1990)), was dissolved in dry dimethylformamide (DMF) (6 mL). Dimethyl-tert-butylsilyl chloride (1.85 g, 12.27 mmol) and imidazole (1.67 g, 24.6 mmol) were added, and the resulting mixture was stirred for 48 hours at 38° C. Water (30 mL) was added, and the mixture was extracted with ether. After evaporation of the dried ether layer, an oil (4b, 3.6 g) was obtained: $[\forall]_D$ 153° (c 24.45 mg/mL, CHCl$_3$); IR $8_{max}$ (neat) 1725 cm$^{-1}$, no free hydroxyl groups were observed; $^1$H NMR (CDCl$_3$) $\Delta$ 3.28 (1 H, br d, J=16Hz, C-2 eq H), 4.46 (2 H, s, C-7 H), 5.70 (1 H, m, C-6 H), 6.38 (1 H, d, J=1.5 Hz, arom), 6.42 (1 H, d, J=1.5 Hz, atom). This oil (compound 4b) was used in the next step with no further purification.

A solution of compound 4b (3.2 g, 5.5 mmol) in dry ether (50 mL) was added under a nitrogen atmosphere to lithium aluminum hydride (870 mg) in dry ether (60 mL). The resulting mixture was boiled under reflux for 1.5 hours. After the standard workup (ethyl acetate followed by slow addition of a saturated solution of magnesium sulfate until a clear supernatant was formed), the ether layer was dried and evaporated to give an oil (3.2 g). The oil was chromatographed on a silica gel column (100 g), using ether-petroleum ether (6:4) as eluent, to give the alcohol 4a (8 g 67%): $[\forall]_D$ −175° (c 7.6 mg/M1, CHCl$_3$); IR $8_{max}$ (neat) 3320 cm$^{-1}$ (OH band), no carbonyl bands; $^1$H NMR (CDCl$_3$) $\Delta$ 3.38 (1 H, br d, J=16Hz, C-2 eq H), 4.02 (2 H, s, C-7 H), 5.72 (1 H, br d, J=16Hz, C-2 eq H), 4.02 (2 H, s, C-7 H), 5.72 (1 H, br d, C-6 H), 6.36, 6.42 (2 H, s, atom).

c. Synthesis of Compound 5b

Following the procedure of Corey and Samuelsson (Corey E. J. and Samuelsson B. "One Step Conversion of Primary Alcohols in the Carbohydrate Series to the Corresponding Carboxylic-Ted-Butyl Esters." J. Org. Chem. 49:4735 (1984)), dry pyridine (2.3 mL) followed by chromic oxide (1.44 g, 14.4 mmol) was added to a solution of methylene chloride-DMF (4:1) (36 mL). The mixture was stirred for fifteen (15) minutes. The primary allylic hydroxy compound 4a (1.8 g, 3.6 mmol) in methylene chloride-DMF (4:1) (7.2 mL) was added, and the reaction mixture was stirred at room temperature for one (1) hour. Ethanol (1.8 mL) was added, and the mixture was stirred for an additional ten (10) minutes and was then diluted with ethyl acetate (180 mL). The resulting mixture was filtered through a sintered-glass funnel, packed with silica (3 cm), with a layer of anhydrous sodium sulfate on top, and eluted with ethyl acetate (ca 600 mL). The ethyl acetate filtrate was washed with dilute hydrochloric acid (1 N) and then with sodium bicarbonate solution and water. After evaporation of the dried organic solvent, a semisolid compound (5b, 1.7 g, 95%) was obtained. Crystallization from pentane gave the aldehyde 5b: mp 80°-81° C.; $[\forall]_D$ −268° (c 6.82 mg/mL, CHCl$_3$), IR $8_{max}$ 1690 cm$^{-1}$ (neat); $^1$H NMR (CDCl$_3$) $\Delta$ 3.82 (1 H, br d, J=15Hz, C-2 eq H), 6.38 and 6.42 (2 H, s, atom), 6.80 (1 H, m, C-6 H), 9.50 (1 H, s, C-7 H). Anal. (C$_{31}$H$_{50}$O$_3$ Si) C, H.

d. Synthesis of (6aR,10aR)-$\Delta^8$-THC-DMH-11-oic Acid (3a)

Following the procedure described by Pellegata et al. (Pellegata R et al. "An Improved Procedure for the Synthesis of Oleuropeic Acid." Synth. Commun. 15:165 (1985)), sodium chloride (488 mg) was added portionwise with vigorous stirring to a mixture of the aldehyde 5b (498 mg, 1 mmol), 2-methyl2-butene (2.24 mL), saturated aqueous potassium dihydrogen phosphate (1.34 mL), and tert-butyl alcohol (22 mL). The reaction mixture was stirred at room temperature for five (5) hours. Water (20 mL) was added, and the mixture was extracted several times with ethyl acetate, dried, and evaporated to give the crude acid which was purified on a silica gel column (10 g, elution with 10% ether-petroleum ether) to give the acid 3b (460 mg, 89%) as an oil: $[\forall]_D$ −218° (c 13.7 mg/mL, CHCl$_3$); IR $8_{max}$ 1680 cm$^{-1}$ and a broad band in the 2800-3600 cm$^{-1}$ region, $^1$H NMR(CDCl$_3$) Δ 3.75 (1 H, br d, J=18Hz, C-2 eq H), 6.23 (1 H, d, J=1.5 Hz, arom), 6.27 (1 H, d, J=1.5 Hz, arom), 7.00 (1 H, br d, C-6 H).

Tetrabutylammonium fluoride (0.6 mmol from a 1.0M solution in THF, Aldrich,) was added by injection under a nitrogen atmosphere to a cold solution (ice bath) of the acid 3b (280 mg, 0.54 mmol) in tetrahydrofuran (THF) (3 mL). The resulting solution was stirred at 0.degree. C. for fifteen (15) minutes. Water was added, and the mixture was extracted several times with ether. The ether layer was dried and evaporated to give the crude product. The product was further purified by silica gel column with ether-petroleum ether (1:1) as eluent. The solid thus obtained (140 mg, 56%) was crystallized from acetonitrile to give the acid 3a: mp 112°-114° C. (sintering); $[\forall]_D$ −275.degree. (c 3.8 mg/mL, CHCl$_3$); IR $8_{max}$ (Nujol) 1680 cm$^{-1}$ and a broad band in the 3100-3600 cm$^{-1}$ region; $^1$H NMR (CDCl$_3$) Δ 3.82 (1 H, br d, J=18Hz, C-2 eq H), 6.22 (1 H, d, J=18Hz, C-2 eq H), 6.22 (1 H, d, J=1.5 Hz, arom), 6.38 (1 H, d, J=1.5 Hz, arom), 7.16 (1 H, m, C-6 , H); m/z 400(M); HRMS calculated for $C_{25}H_{36}O_4$ 400.2613, found 400.2592.

e. Synthesis of (6aR,10aR)-Δ$^8$-THC-DMH-11-oic Acid Acetate (3c)

A solution of acid 3a (100 mg, 0.25 mmol) in pyridine (2 mL) and acetic anhydride (1 mL) was stirred overnight at room temperature. Water (5 mL) was added to hydrolyze any mixed anhydride formed. The mixture was stirred for two (2) hours and then partitioned between water and ether. The ether layer was washed with dilute HCl (to remove the pyridine) and water. The organic layer was dried and evaporated. Pure product was obtained by preparative TLC (eluent ether-petroleum ether, 60:40) and crystallization from pentane. The acetate 3c, 65 mg, melts at 120°-122° C.: $[\forall]_D$ −265° (c 9.0 mg/mL, CHCl$_3$); IR $8_{max}$, (Nujol) 1760 cm$^{-1}$ and a broad band in the 3100-3600 cm$^{-1}$ region; $^1$H NMR (CDCl$_3$) Δ 2.30 (3 H, s, OCOCH$_3$), 3.38 (1 H, br d, J=19Hz, C-2 eq H), 6.56 (1 H, d, J=1.5 Hz, atom), 6.68 (1 H, d, J=1.5 Hz, arom), 7.18 (1 H, m, C-6, H); HRMS calculated for $C_{27}H_{38}O_4$ 442.2719, found 442.2691.

f. Preparation of Capsules

A large number of unit capsules are prepared by filling standard two-piece hard gelatin capsules each with the desired amount of the powdered active ingredient as described above, 150 milligrams of lactose, 50 milligrams of cellulose, and 6 milligrams magnesium stearate. The capsules may also be prepared to include existing compounds useful in treating interstitial cystitis, and/or anticholinergic agents.

g. Preparation of Soft Gelatin Capsules

A mixture of active ingredient in a digestible oil such as soybean oil, lecithin, cottonseed oil or olive oil is prepared and injected by means of a positive displacement pump into gelatin to form soft gelatin capsules containing the desired amount of the active ingredient. The capsules are washed and dried for packaging. The soft gelatin capsules may also be prepared to include existing compounds useful in treating interstitial cystitis, and/or anticholinergic agents.

h. Preparation of IVI Formulation

A formulation suitable for administration via intravesicular instillation is prepared by dissolving the desired amount of the active ingredient as described above in a suitable volume of saline. The formulation may also be prepared to include existing compounds useful in treating interstitial cystitis, and/or anticholineric agents. Preferably, because the active ingredient may be relatively insoluble in water, it may be advantageously incorporated into liposomes.

The Effects of (6aR,10aR)-Δ$^8$-Tetrahydrocannabinol-11-oic Acids (and their Esters) on Bladder Overactivity Induced by Acute and Subacute Bladder Irritation in Rats Cystometrograms (CMGs) were performed under urethane anesthesia (1 g/kg s.c.) using a catheter inserted into the bladder through the bladder dome via a midline abdominal incision. Saline was infused at a rate of 0.04 ml/min to elicit repetitive bladder contractions. Effects of intravenous (i.v.) injection of Compound 3a on bladder overactivity induced by either intravesical administration of acetic acid solution or one day treatment with cyclophosphamide were investigated. As discussed further, below, Compound 3a at a preferred dose of 10 mg/kg significantly suppressed bladder overactivity induced by acetic acid infusion (acute model) and administration of cyclophosphamide (subacute model) without affecting bladder contractility. These results indicate that (6aR,10aR)-Δ$^8$-tetrahydrocannabinol-11-oic acids (and their esters) can suppress bladder nociceptive responses induced by bladder irritation, probably due to suppression of bladder sensory activity. Thus, these compounds can be effective for the treatment of pain and urinary frequency symptoms in patients with painful bladder syndrome/interstitial cystitis.

i. Acute Bladder Irritation by Acetic Acid (AA) Infusion

Saline infusion was performed for 1 to 2 hours prior to drug (or vehicle) administration and control CMGs were recorded. Compound 3a (aka CT-3 or IP-751, dissolved in 30% Cremophor EL saline solution; three concentrations of 1, 3, and 10 mg/kg) or vehicle was administrated intravenously when starting infusion of acetic acid solution (0.25%) into the bladder.

Changes in cystometric parameters such as intercontraction intervals (ICIs), maximum voiding pressure (MVP), pressure threshold (PT) and baseline pressure (BP) were evaluated before and after i.v. administration of Compound 3a or vehicle.

In the vehicle group, 0.25% acetic acid infusion induced significant bladder overactivity, as evidenced by a reduction in ICIs to 42.9% of the control value. This reduction in ICIs was suppressed by Compound 3a, preferably at a dose of 10 mg/kg, giving rise to an ICI that was 112.4% of the control value (P<0.05, n=6). Lower doses of Compound 3a (1 mg/kg and 3 mg/kg—giving rise to ICI values of 45.2% and 51.1% of the control value, respectively) were less effective. Compound 3a (or its acetate ester, a prodrug of 3a) at a dose of 10 mg/kg is also expected to increase the pressure threshold to 127.2% of the control value while vehicle, 1 mg/kg, or 3 mg/kg of Compound 3a did not have such increases (87.1%, 74.1%, 94.1% of the control value, respectively). No significant changes in MVP and BP were observed. Thus, Compound 3a, preferably at 10 mg/kg (i.v.), significantly suppressed acetic acid-induced bladder overactivity without affecting bladder contractions during voiding. The results are shown in FIGS. 2-5.

j. Subacute Bladder Irritation by Cyclophosphamide

One day after intraperitoneal injection of cyclophosphamide (CYP, 150 mg/kg), control CMGs were recorded for 1 to 2 hour prior to i.v. administration of Compound 3a or vehicle. See, example i, above. Following administration of Compound 3a, changes in cystometric parameters such as ICIs, MVP, PT and BP were recorded to evaluate the effects of Compound 3a on cyclophosphamide-induced bladder overactivity.

Figure 6:
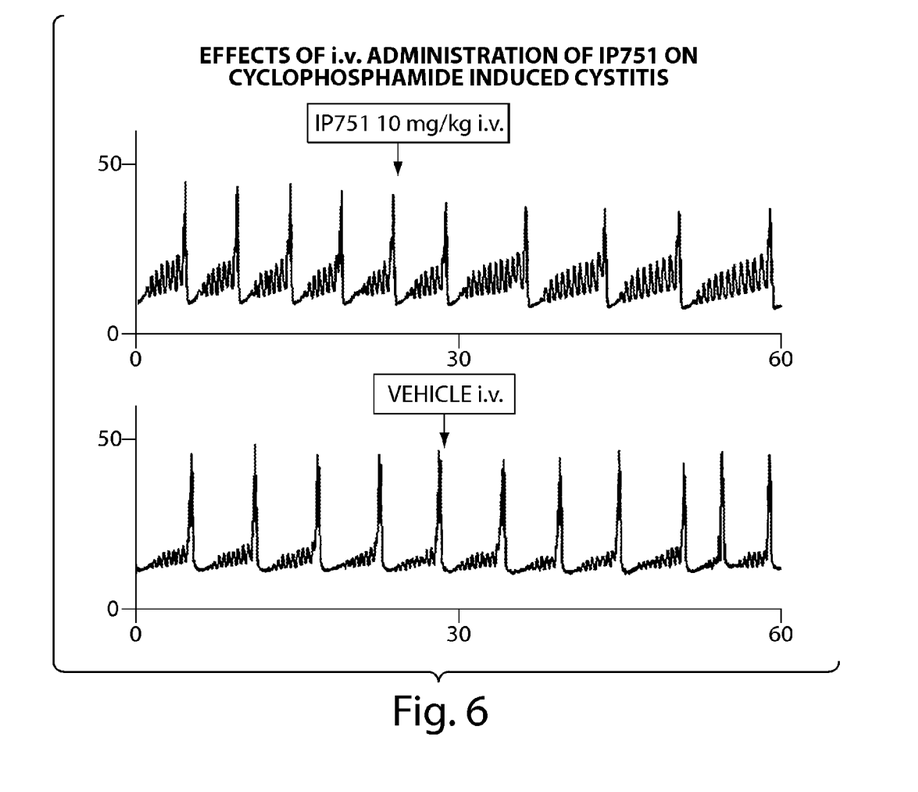
FIG. 6 shows cystometrograms relating to Example j.
Figure 7:
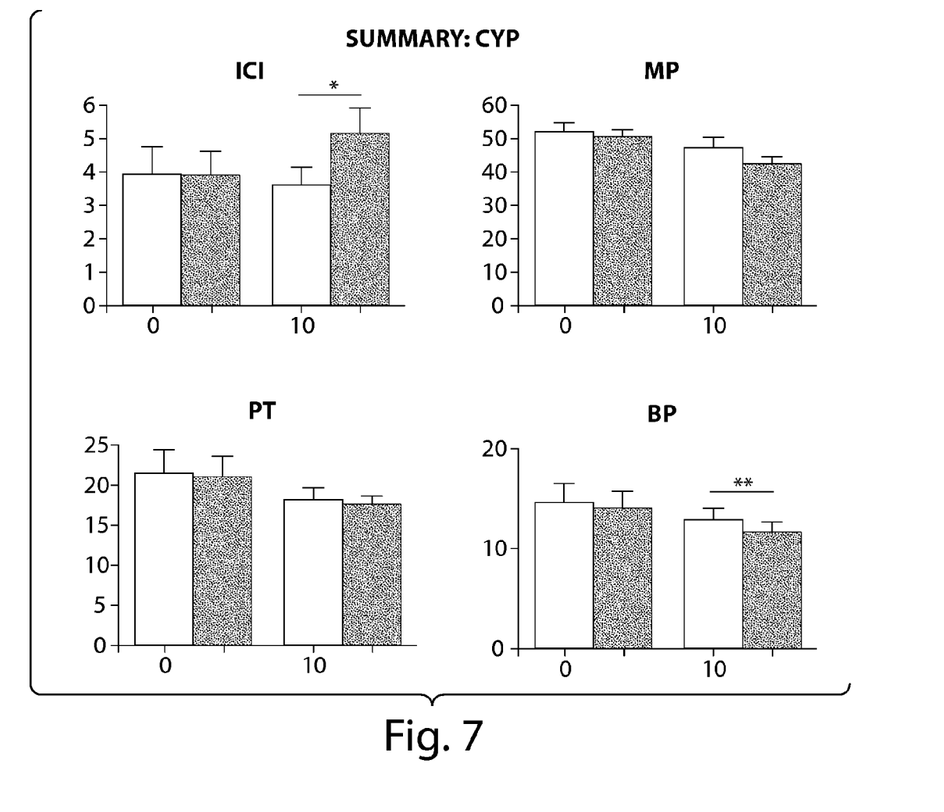
FIG. 7 is a summary of results of Example j.
Figure 8:
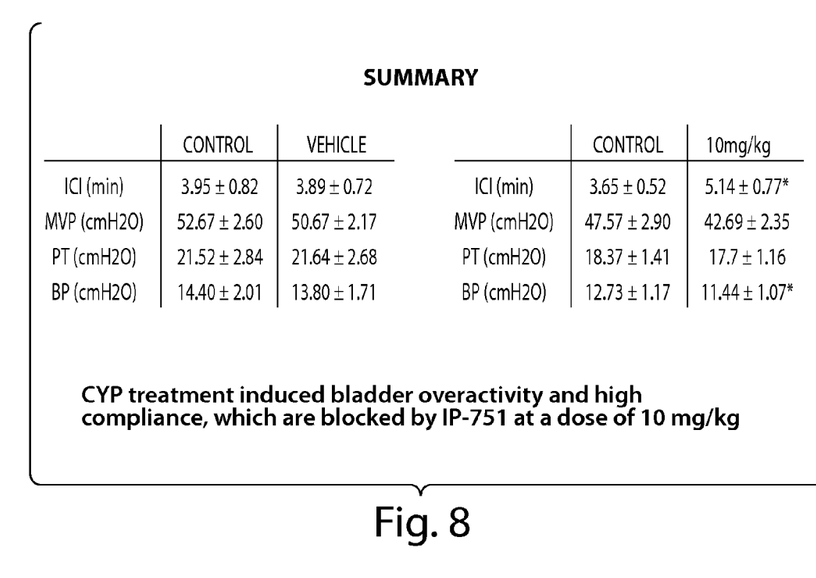
FIG. 8 is a summary of the numerical results of Example j.

Bladder overactivity indicated by significant ICI reductions was observed one day after CYP injection. Administration of Compound 3a at a dose of 10 mg/kg (i.v.) significantly suppressed CYP-induced bladder overactivity as evidenced by the increment of ICIs to 5.14 min from control value (3.65 min) while vehicle did not alter ICIs (3.89 vs. 3.94 min) in CYP-treated rats. No significant changes were observed in MVP, PT and BP after IP-751 administration in CYP-treated rats. The results are shown in FIGS. 6-8.

Intravesical Administration of Compound 3a Using Liposomes as a Delivery Vehicle (Observation of Biological Activity at 24Hours and 48Hours Post-Administration)

Cyclophosphamide (100 mg/kg) was injected intraperitoneally into test rats 12 hours before the start of transurethral open cystometry under urethane anesthesia. CMGs were recorded while saline was instilled intravesically (that is, intravesicularly) for 1 hour. Afterwards, a saline solution of Compound 3a (0.24 mg/ml) entrapped in liposomes was instilled similarly. Comparison of the resulting CMGs revealed a significant reduction in bladder contraction frequency after infusion of the saline solution of Compound 3a/liposomal mixture compared with simple saline (P<0.01, n=7).

Similarly, instillation of liposomal-Compound 3a was first conducted. Then, 24 hours and 48 hours after instillation, under urethane anesthesia, bladder hyperactivity was induced by infusing acetic acid at the concentration of 0.125% and 025%. Prior to acetic acid infusion, baseline CMG was conducted by saline infusion (0.04 ml/min) to measure intercontraction interval (ICI). A percentage reduction in ICI was measured following acetic acid infusion as an indicator of bladder irritation. The results, described further below, indicated that the percentage reduction in ICI is lower in animals instilled with liposomal-Compound 3a 24 hours and 48 hours prior to acetic acid infusion, compared to the same protocol in the absence of drug (control saline and control empty liposome).

Figure 9A:
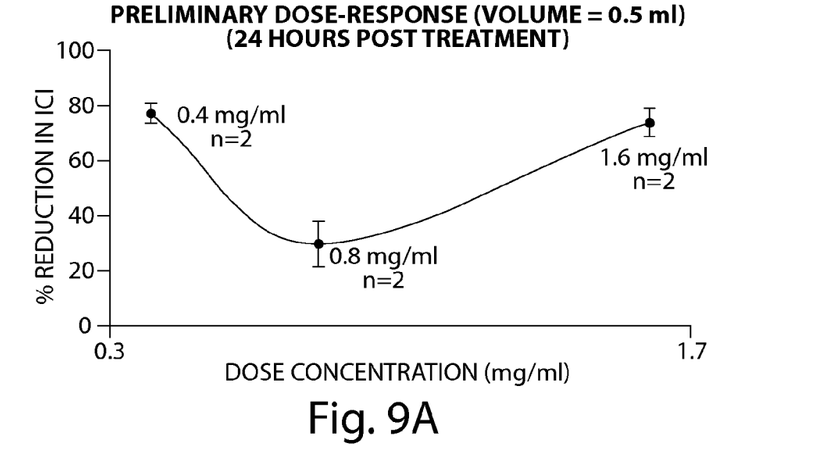
FIGS. 9A-9C show a preliminary dose-response curve, response to acetic acid 24 hours post drug treatment, and response to acetic acid 48 hours post drug treatment.
Figure 9B:
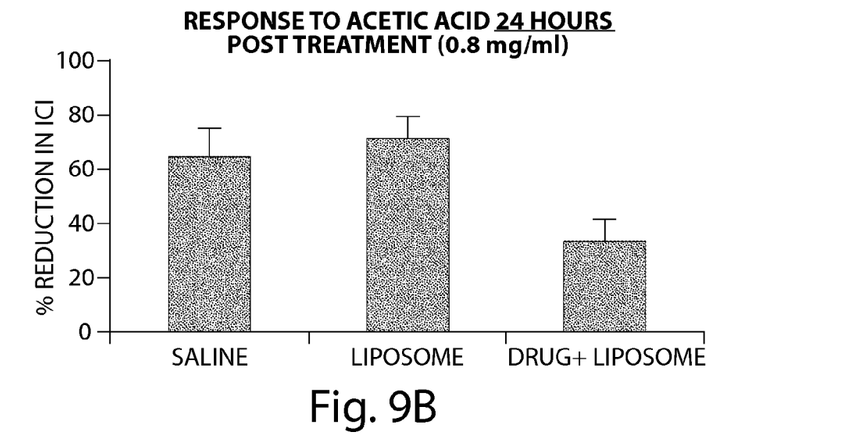
Figure 9C:
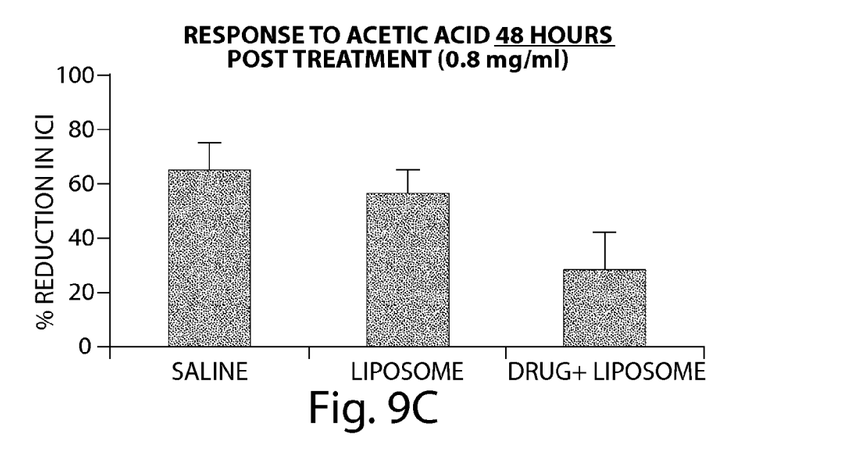

ICI reductions in the treatment groups were approximately 50% lower then those of the control groups (saline and empty liposome), suggesting an effective response at both the 24-hour and 48-hour time points. See, FIGS. 9B and 9C, respectively. Each group consisted of a minimum of seven subjects, except for those of a preliminary dose response study, where two subjects were used in each group. The preliminary dose response study indicated an optimal Compound 3a dose of 0.8 mg/ml. See, FIG. 9A. In these experiments, 1.6 mg/ml was highest concentration of Compound 3a encapsulated into liposomes; higher concentrations apparently compromised formulation stability.

Comparable results are obtained using any of the compounds of the invention including, but not limited to, Compounds 3a, 3b, 3c, 3d, 3e, their prodrugs (e.g., esters) and pharmaceutically acceptable salts or solvates thereof. Comparable results are also obtained using other models of bladder overactivity using irritants including, but not limited to, nerve growth factor and protamine sulfate.

Conclusion

Those skilled in the art will recognize, or be able to ascertain using no more than routine experimentation, many equivalents to the specific embodiments of the invention described herein. Such equivalents are intended to be encompassed by the following claims.

What is claimed is:

1. A method of treating mammals suffering from interstitial cystitis using a compound having Formula III Formula III or a pharmaceutically acceptable salt thereof, the method comprising: identifying a mammal suffering from or suspected of suffering from interstitial cystitis; and administering to the mammal an effective amount of the compound of Formula III.

2. The method of claim 1, wherein the mammal is a human.

3. The method of claim 1, wherein the compound is administered orally.

4. The method of claim 1, wherein the compound is administered via intravesicular instillation.

5. The method of claim 1, wherein the compound is administered via an implant.

6. The method of claim 5, wherein the implant provides slow release of the compound.

7. The method of claim 1, wherein the compound is administered intravenously.

* * * * *